United States Patent [19]

Navarrini et al.

[11] Patent Number: 5,103,051
[45] Date of Patent: * Apr. 7, 1992

[54] PROCESS FOR PREPARING PERFLUOROALKENYL-SULFONIL FLUORIDES

[75] Inventors: Walter Navarrini; Silvana Modena, both of Milan, Italy

[73] Assignee: Ausimont S.r.l., Milan, Italy

[ * ] Notice: The portion of the term of this patent subsequent to Apr. 7, 2009 has been disclaimed.

[21] Appl. No.: 515,176

[22] Filed: Apr. 26, 1990

[30] Foreign Application Priority Data

Apr. 28, 1989 [IT] Italy ................... 20340 A/89

[51] Int. Cl.$^5$ ............................................ C07C 315/04
[52] U.S. Cl. ........................................................ 562/825
[58] Field of Search ............................. 562/825, 834

[56] References Cited

U.S. PATENT DOCUMENTS 3,041,317 6/1962 Gibbs et al. ............... 562/825
4,834,922 5/1989 Ezzell et al. .............. 562/825

FOREIGN PATENT DOCUMENTS 60-36454 2/1985 Japan ..................... 562/825

OTHER PUBLICATIONS

Kirk-Othmer, *Encyclopedia of Chem. Technology*, pp. 414–417.

Primary Examiner—Alan Siegel
Assistant Examiner—Margaret Argo
Attorney, Agent, or Firm—Stevens, Davis, Miller & Mosher

[57] ABSTRACT

A continuous process for preparing perfluoroalkenyl sulfonyl fluorides (I)

$$R_f-CF=CF-SO_2F \qquad (I)$$

wherein $R_f$ is selected from the group consisting of F and a perfluoroalkyl of from 1 to 9 carbon atoms is disclosed, in which a perfluoroalkyl (sulfonyl fluoride) monofluoroacetyl fluoride of formula $$R_f-CF_2-CF(COF)SO_2F \qquad (II)$$

is used as the starting product.

The starting product is contacted with a reactant selected from the group consisting of the oxides of an element of the Groups IA, IIA, IIB, IIIA and IVA of the Periodic Table of the Elements, and of their mixtures, at a temperature comprised within the range of from 150° to 450° C., and the compound (I) is recovered from the reaction effluent.

8 Claims, No Drawings

PROCESS FOR PREPARING PERFLUOROALKENYL-SULFONIL FLUORIDES

DESCRIPTION OF THE INVENTION

The present invention relates to a new process for the synthesis of perfluoroalkenyl sulfonyl fluorides, in particular of perfluorovinyl sulfonyl fluoride.

These perfluorinated compounds, which contain the sulfonyl function, are monomers useful for preparing high-molecular-weight polymers, which find several uses.

In U.S. Pat. No. 3,041,317, a process is disclosed for the synthesis of perfluoroalkenyl-sulfonyl fluorides of formula $$R_f\text{—CF}=\text{CF—SO}_2F$$

wherein $R_f$ is F, or a perfluoroalkyl radical or an omega-hydroperfluoroalkyl radical. The starting products for the above mentioned synthesis are 2-hydro-perfluoroalkyl-sulfonyl fluorides of general formula $$R_f\text{—CF}_2\text{—CFH—SO}_2F$$

which are dehydrofluorinated in order to yield perfluoroalkenyl-sulfonyl fluorides in a plant operating under reduced pressure, inside which a stream of reactants flows on a catalyst constituted by chrome oxide supported on KCl, at temperatures comprised within the range of from 450° to 630° C.

In particular for vinyl-sulfonyl fluoride, the reaction is carried out at temperatures comprised within the range of from 508° to 517° C. with a conversion of 51% and a yield of 61%, as referred to the converted reactants, per each individual pass.

R. E. Banks in J. Chem. Soc. (C), 1966 reports about a synthesis of perfluorovinyl-sulfonyl fluoride, in which synthesis a catalyst and operating conditions are used, which are exactly the same as those disclosed in U.S. Pat. No. 3,041,317, with the only difference that the catalytic bed is pre-heated at 510° C. before the synthesis test is carried out.

In the paper by R. E. Banks, the general reactivity of the same molecule is furthermore described.

In both of the above descriptions, the starting products are 2-hydro-perfluoro-sulfonyl fluorides having the general formula $$R_f\text{—CHF—CF}_2\text{—SO}_2F$$

which are synthetized by means of the controlled hydrolysis of the relevant sultones of formula

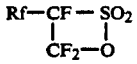

as taught by D. C. England in J. Amer. Chem. Soc. 1960, 82, 6181.

The main object of the present invention is of providing a new process for preparing perfluoroalkenyl-sulfonyl fluorides, which process can be carried out under advantageous temperature and pressure conditions from the economic viewpoint, as compared to the processes known from the prior art.

Another object of the present invention is of providing a simplified process, which does not require additional steps, such as, e.g., steps of hydrolysis of sultonic precursors, as in the processes of the prior art.

A further object is of providing a process which uses easily available and cheap catalysts.

Finally, still a further object of the present invention is of providing a process which supplies high yields of the desired perfluoroalkenyl-sulfonyl fluorides.

These and still other objects which will be clear from the following disclosure are achieved by a process, according to the instant invention, for preparing perfluoroalkenyl sulfonyl fluorides having the general formula (I)

$$R_f\text{—CF}=\text{CF—SO}_2F \quad (I)$$

wherein: $R_f$ is selected from the group consisting of F and a perfluoroalkyl radical of from 1 to 9 carbon atoms, which process consists in bringing into contact a starting compound comprising a perfluoroalkyl (sulfonyl fluoride) monofluoroacetyl fluoride of formula $$R_f\text{—CF}_2\text{—CF(COF)SO}_2F \quad (II)$$

with a reactant selected from the group consisting of oxides of an element of the Groups IA, IIA, IIB, IIIA and IVA of the Periodic Table of the Elements, and of their mixtures, at a temperature comprised within the range of from 150° to 450° C., and recovering the desired compound of formula (I) from the reaction effluent.

The starting compound (II) is obtained by means of the isomerization of the corresponding sultone in the presence of catalytic amounts of KF or of trialkylamines, with quantitative yields, according to as described by D. C. England in J. American Chem. Soc. 1960, 82, 6181.

The reactant used in the instant process is constituted by one or more oxide(s) of the above mentioned elements, among which CaO, SiO$_2$, MgO and ZnO can be cited for exemplifying purposes.

The reactions on which the instant invention process is based can be illustrated for exemplifying purposes, relatively to the use of CaO as the reactant, as follows:

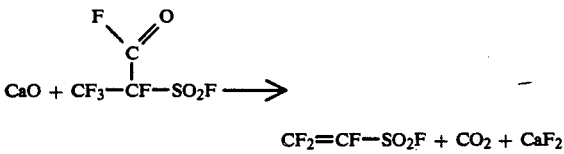

The amount of reactant used in the reaction is at least equal to the stoichiometric amount required by the above reaction, but it is preferably in a substantial excess over said stoichiometric amount, being also a function of the degree of fineness of the particles of the solid reactant used in the reaction.

The reactant is advantageously submitted to a preliminary activation by being placed into contact with the starting compound before the true process is started.

The process according to the present invention can be advantageously carried out in continuous under atmospheric pressure, although also pressures lower or higher than atmospheric pressure can be used as well.

The process temperature can be comprised within the range of from 150° to 450° C., and is preferably comprised within the range of from 180° to 280° C.

The process is suitably carried out by causing a stream of an inert gas carrier, saturated with vapours of the used starting compound to flow on a bed of the reactant contained inside a glass or steel column reactor.

As the inert gas carrier, nitrogen is preferably used.

The process is carried out under anhydrous conditions, with both nitrogen and the reactant bed being preliminarily thoroughly dried; this latter, by being heated at about 300°-330° C. for a few hours.

In the reactor, a packing of a particulate, e.g. silicious, material with small particle size, is preferably used in addition to the reactant bed.

Flow rate values of the carrier and reactant stream are used, such as to secure a stay time of from 3 to 30 seconds of the starting compound inside the reactor.

The effluent from the reactor is condensed at a temperature comprised within the range of from 0° to −196° C. in order to separate the reaction products from nitrogen, which is sent to the discharge stack.

The condensate is distilled under reduced pressure, e.g., under a pressure of about $10^{-3}$ torr, and the vapours are condensed in a first condenser at a temperature of, e.g., from −100° C. to −20° C. in order to recover the resulting desired perfluoroalkenyl-sulfonyl fluoride, and then in a second condenser at −110° C. in order to recover the produced $SO_2$.

The other byproducts, such as $CO_2$ and, possibly, $SiF_4$, as well as any decomposition products, such as $CF_3COF$ or $C_2F_4$, are removed by the dynamic vacuum during the same distillation.

Complete conversions of the starting compound are obtained, with high yields, of the order of from 65 to 75%, which yields are defined as the ratio of the mols of the resulting desired product to the reacted mols of starting compound.

The process according to the present invention is particularly useful in order to prepare compounds of formula (I), wherein $R_f$ is F or a perfluoroalkyl radical of from 1 to 3 carbon atoms, in particular a trifluoromethyl or perfluoroethyl radical.

The following examples are illustrative of preferred forms of embodiment of the present invention, and in no way such examples should be construed as being limitative of the scope of the present invention, as herein disclosed and as claimed in the hereto appended claims.

EXAMPLE I

In a continuous working plant 3.15 g (13.5 mmol) of 2,3,3,3-tetrafluoro-2-(fluorosulfonyl)-propionyl fluoride

$CF_3$—$CF(COF)$—$SO_2F$ is charged to a loading "U"-shaped trap.

Said loading trap is then put into communication with the continuous working plant by means of valves.

A stream of preliminarily thoroughly dried nitrogen is made flow at the flowrate of 10 litres/hour through the loading trap, which is kept at the temperature of 0° C. throughout the test time.

Nitrogen saturated with the vapours of the starting product flows through the reactor kept at the temperature of 200° C.

During about 2 hours, all of the starting product is transported through the reactor, which is constituted by a steel column of 3.0 cm of diameter, packed with 100 g of calcium oxide and 100 g of steel small tubes; the so constituted reactant bed is preliminarily thoroughly dried by being kept at the temperature of 320° C. for 4 hours, and is then activated by causing 13.5 mmol of the starting product to preliminarily flow through it under the same operating conditions as disclosed hereinabove.

The effluent gases from the reactor are caused to flow through two traps maintained at the temperature of −196° C. so as to condense all of the reaction products, whilst, on the contrary, nitrogen carrier gas flows to the discharge stack.

The raw reaction product contained inside the two collection traps is distilled under the pressure of $10^{-3}$ torr. The vapours coming from the still kettle are caused to flow through cold traps respectively kept at the temperatures of −80° and −110° C.

Inside the trap at −110° C., $SO_2$ condenses; in the traps at −80° C. the desired product trifluorovinyl-sulfonyl fluoride

$CF_2$=$CF$—$SO_2F$ condenses. $CO_2$, and any decomposition products, such as, e.g., $CF_3COF$ and $C_2F_4$ are removed by the dynamic vacuum during the same distillation.

The conversion of the starting product is complete.

The yield, defined as the ratio of the mols of the desired product ($CF_2$=$CF$—$SO_2F$) to the reacted mols of the starting product, is of 65%.

EXAMPLE II

By means of modalities identical to those of Example I, 3.15 g (13.5 mmol) of 2,3,3,3-tetrafluoro-2-(fluorosulfonyl)propionyl fluoride

$CF_3$—$CF(COF)$—$SO_2F$ is made flow through the reaction plant, with the temperature of the addition trap being kept at 0° C. throughout the test time.

During about 2 hours, all of the starting product flows through the reactant bed of MgO, activated in the same way as disclosed in Example I, and maintained at the temperature of 200° C.

The flow rate of carrier nitrogen stream is kept at 8 litres/hour throughout the test time.

The conversion of the starting product is of 30%. The reaction yield, defined as in Example I, is of 63%.

What is claimed is:

1. A process for preparing perfluoroalkenyl sulfonyl fluorides having the formula (I)

$R_f$—$CF$=$CF$—$SO_2F$    (I)

wherein: $R_f$ is selected from the group consisting of F and a perfluoroalkyl radical of from 1 to 9 carbon atoms, comprising contacting a perfluoroalkyl (sulfonyl fluoride) monofluoroacetyl fluoride of formula

$R_f$—$CF_2$—$CF(COF)SO_2F$    (II)

wherein $R_f$ has the meaning defined above, under anhydrous reaction conditions with a reactant selected from the group consisting of oxides of an element of Group IA, IIA, IIB, IIIA and IVA of the Periodic Table of the Elements, and their mixtures, at a temperature range of from 150° to 450° C., and recovering the desired compound of formula (I) from the reaction effluent.

2. Process according to claim 1 wherein $R_f$ is F.

3. Process according to claim 1 wherein $R_f$ is a perfluoroalkyl radical of from 1 to 3 carbon atoms.

4. Process according to claim 1 carried out continuously under atmospheric pressure.

5. Process according to claim 1 wherein said reactant is selected from the group consisting of CaO, MgO, ZnO and $SiO_2$.

6. Process according to claim 1 wherein said temperature is within the range of from 180° to 280° C.

7. Process according to claim 1 wherein said contacting step is carried out by causing a stream of an inert carrier gas saturated with the vapors of said perfluoroalkyl-(sulfonyl fluoride) monofluoroacetyl fluoride to flow on to the reactant.

8. Process according to claim 7 wherein said inert gas carrier is nitrogen.

* * * * *